United States Patent
Richardson et al.

(10) Patent No.: US 6,177,276 B1
(45) Date of Patent: Jan. 23, 2001

(54) OXIDATION AND MEASUREMENT OF PHOSPHONATES IN AQUEOUS SOLUTIONS

(75) Inventors: John Richardson, Mechanicsville; Michael G. Trulear, Richmond, both of VA (US)

(73) Assignee: ChemTreat, Inc., Ashland, VA (US)

( * ) Notice: Under 35 U.S.C. 154(b), the term of this patent shall be extended for 0 days.

(21) Appl. No.: 08/991,051

(22) Filed: Dec. 16, 1997

(51) Int. Cl.⁷ .................................................. G01N 31/00
(52) U.S. Cl. ........................ 436/55; 436/103; 436/104; 436/175; 436/178
(58) Field of Search ................................. 436/103, 104, 436/175, 178, 55

(56) References Cited

U.S. PATENT DOCUMENTS

| | | | |
|---|---|---|---|
| 4,108,746 | 8/1978 | Mill et al. ............................ | 204/158 |
| 4,783,314 | 11/1988 | Hoots et al. ............................ | 422/3 |
| 5,242,602 | 9/1993 | Richardson et al. ................. | 210/745 |
| 5,270,216 | 12/1993 | Kan et al. ............................ | 436/103 |
| 5,702,954 | * 12/1997 | Stedman et al. ..................... | 436/103 |

OTHER PUBLICATIONS

Blystone et al., "A Rapid Method for Analysis of Phosphonate Compounds" Hach Company, pp. 245–250.

Rice et al., "Fundamental Aspects of Ozone Chemistry in Recirculating Cooling Water Systems", The NACE Annual Conference and Corrosion Show, Paper No. 205, (1991), pp. 205/2–205/43.

Hollingshad et al., "The Effect of Ozone on Traditional Cooling Water Treatment Chemicals" The NACE Annual Conference and Corrosion Show, Paper No. 348, (1992), pp. 348/2–348/15.

* cited by examiner

Primary Examiner—Jill Warden
(74) Attorney, Agent, or Firm—Foley & Lardner

(57) ABSTRACT

The invention provides methods and apparatuses for oxidizing phosphonate in an aqueous solution, for determining the concentration of phosphonate present in an aqueous solution, and for controlling the concentration of phosphonate present in an aqueous solution. Optionally, one or more computers are used to automate the methods.

18 Claims, 2 Drawing Sheets

Diagram of Cooling Tower Phosphonate Analyzer

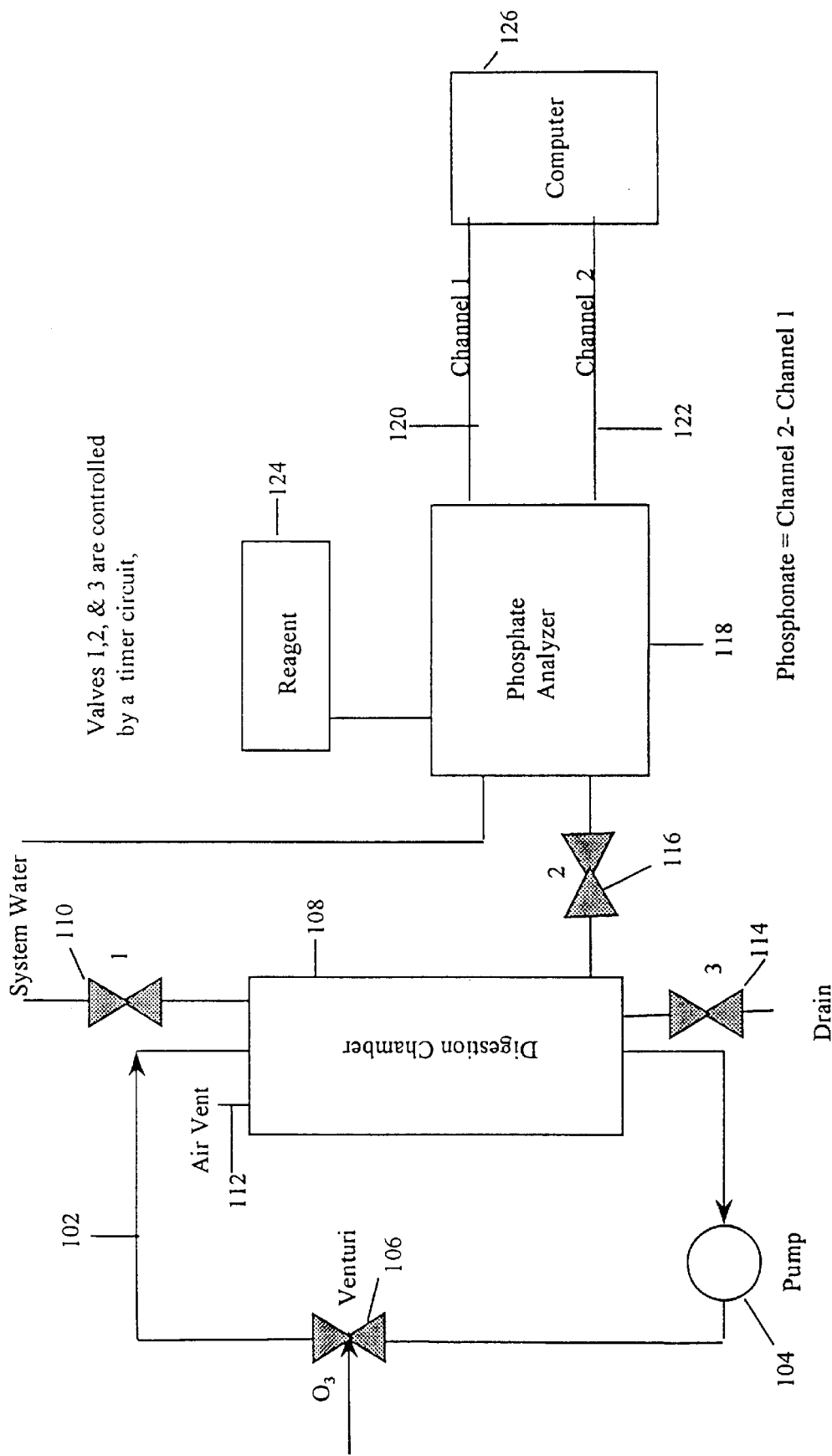
Fig 1. Diagram of Cooling Tower Phosphonate Analyzer

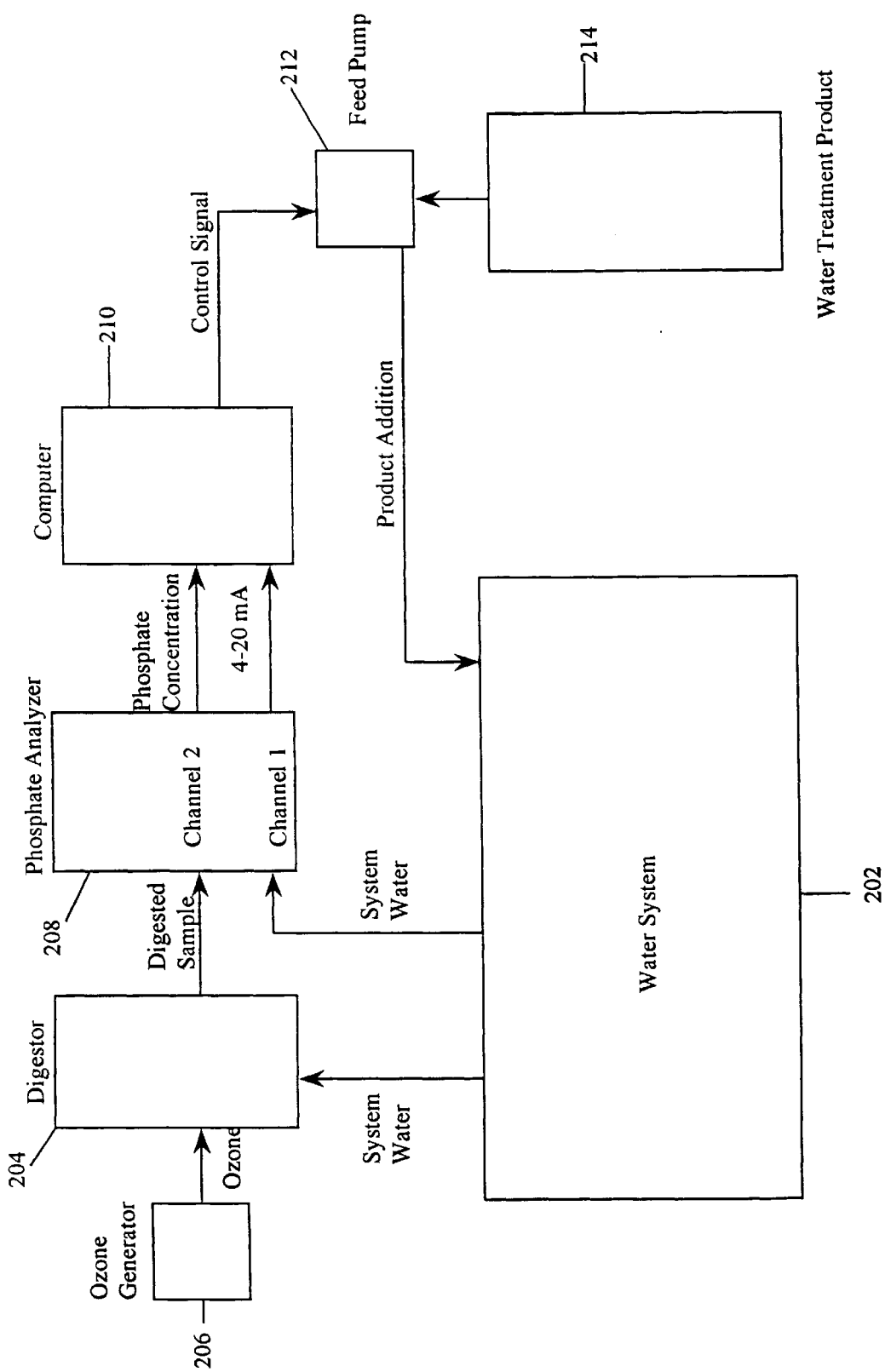
Fig. 2 Flow Diagram of Phosphonate Monitor and Control Apparatus

OXIDATION AND MEASUREMENT OF PHOSPHONATES IN AQUEOUS SOLUTIONS

FIELD OF THE INVENTION

The present invention is directed to a method and apparatus for oxidizing phosphonates present in an aqueous solution and a method and apparatus for determining the concentration of phosphonates present in an aqueous solution. Methods and apparatus for monitoring, controlling and optimizing the concentration of phosphonates present in an aqueous solution also are provided.

BACKGROUND OF THE INVENTION

Phosphonates are compounds which are used in water treatment systems to control scale formation and corrosion. The concentration of phosphonates in the water must be maintained within specific limits in order to optimize and maintain the water treatment system's performance. Too little phosphonate in the water will lead to scale formation, while too much phosphonate may cause corrosion. Using more phosphonate than needed to prevent scale formation also is a waste of phosphonate.

Currently, the concentration of phosphonate present in the water of a water treatment system is typically measured in one of two ways. The most conventional method relies on the analysis of grab samples. That is, a sample of water is withdrawn from the system and analyzed by conventional manual techniques. For example, the phosphonate in the water sample is oxidized to phosphate using UV light and a chemical oxidizing agent such as potassium persulfate. The concentration of phosphate then is measured colorometrically, and correlated to the concentration of phosphonate present in the original sample. See Blystone et al., *Internat'l Water Conference,* Pittsburgh, Pa. (1981). As used herein, the term "grab sample method" refers to the above-described method wherein a sample of water is withdrawn from the system and a chemical oxidizing agent is used in a wet bench laboratory analysis of the phosphate/phosphonate content. Grab sample methods are labor intensive, subject to human error, and take about 15 minutes for each grab sample. They cannot be automated readily because potassium persulfate is hazardous, not stable, and would have to be replaced as it is degraded.

Another method for determining the concentration of phosphonate present in the water of a water treatment system uses inert tracers. In this method, an inert tracer that can be easily measured spectroscopically, such as a fluorescent compound, is added to the system water in a fixed ratio to the amount of phosphonate added to the system water. The level of tracer in the system water is measured from time to time and correlated to the concentration of phosphonate present in the system water. U.S. Pat. No. 4,783,314 describes an example of this type of method. This tracer method suffers from several drawbacks. First, this method measures only the concentration of tracer in the system water, and assumes that the ratio of tracer to phosphonate remains constant throughout the system. Because phosphonate is an active ingredient (and may decompose, precipitate, or be adsorbed), whereas the tracer is inert, this assumption may not be a valid one. Second, because the level of phosphonate itself is not determined, errors resulting from a failure of this assumption are not detected. Phosphonates cannot be measured directly by this method because they are not easily detectable spectroscopically.

Accordingly, there is a need for a method for determining the concentration of phosphonate present in an aqueous solution that is simple, accurate, and subject to automation.

OBJECTS OF THE INVENTION

It is therefore one object of the present invention to provide a method and apparatus for oxidizing phosphonates that does not require a chemical oxidizing agent such as potassium persulfate.

It is another object of the present invention to provide a method and apparatus for determining the concentration of phosphonate present in an aqueous solution that is simple, accurate, and readily automated.

It is another object of the present invention to provide an automated method and apparatus for controlling the concentration of phosphonate present in an aqueous solution.

It is yet another object of the present invention to provide a method and apparatus for optimizing the concentration of phosphonate present in an aqueous solution.

In accordance with these and other objects, the present invention provides the following methods and apparatuses.

In accordance with one aspect, the present invention provides a method for oxidizing phosphonate in an aqueous solution, comprising (A) pumping the solution through a recirculating loop; (B) introducing ozone into the loop through a venturi injector; and (C) digesting the solution with ozone in a digestion chamber.

In accordance with another aspect, the present invention provides a method for determining the concentration of phosphonate present in an aqueous solution, comprising (A) reacting a first sample of the solution with ozone, thereby forming an oxidized first sample comprising phosphate; (B) measuring the concentration of phosphate present in the oxidized first sample; (C) measuring the concentration of phosphate present in a second sample of the solution; (D) subtracting the concentration of phosphate in the second sample from the concentration of phosphate in the oxidized first sample, and using this difference to determine the concentration of phosphonate present in the aqueous solution. Optionally, one or more computers are used to automate this method.

In accordance with another aspect of the present invention, there is provided a method for determining the concentration of phosphonate present in an aqueous solution, comprising (A) diverting a first sample of the aqueous into a recirculation loop; (B) introducing ozone into the loop through a venturi injector; (C) digesting the first sample with ozone in a digestion chamber; (D) recirculating the first sample through the recirculation loop until at least about 90% of the phosphonate present in the first sample is oxidized to phosphate; (E) introducing the oxidized first sample to a phosphate analyzer; (F) measuring the concentration of phosphate present in the oxidized first sample; (G) introducing a second sample of the aqueous solution into a phosphate analyzer; (H) measuring the concentration of phosphate present in the second sample; (I) subtracting the concentration of phosphate in the second sample from the concentration of phosphate in the oxidized first sample, and using this difference to determine the concentration of phosphonate present in the aqueous solution.

In accordance with another aspect of the invention, there is provided a method for controlling the concentration of phosphonate present in an aqueous solution, comprising (A) reacting a first sample of the aqueous solution with ozone, thereby forming an oxidized first sample comprising phosphate; (C) measuring the concentration of phosphate present in the oxidized first sample; (D) measuring the concentration of phosphate present in a second sample of the aqueous solution; (E) subtracting the concentration of phosphate in the second sample from the concentration of phosphate in the oxidized first sample, and using this difference to determine the concentration of phosphonate present in the aqueous solution; (F) comparing the concentration of phosphonate present in the solution to a predetermined target concentration; and (G) if the concentration of phosphonate present in the solution is less than the target concentration, increasing the concentration of phosphonate in the solution; or (G') if the concentration of phosphonate present in the solution is more than the target concentration, reducing the concentration of phosphonate in the solution. Optionally, one or more computers are used to automate this method.

In accordance with another aspect of the invention, there is provided a method for continually optimizing the concentration of phosphonate in an aqueous solution contained in an apparatus, comprising (A) observing the apparatus for scale formation or corrosion; (B) if scale formation is observed, increasing a predetermined target concentration of phosphonate present in the solution to establish a new target concentration; or (B') if corrosion is observed, decreasing a predetermined target concentration of phosphonate present in the solution to establish a new target concentration; (C) reacting a first sample of the aqueous solution with ozone, thereby forming an oxidized first sample comprising phosphate; (D) measuring the concentration of phosphate present in the oxidized first sample; (E) measuring the concentration of phosphate present in a second sample of the aqueous solution; (F) subtracting the concentration of phosphate in the second sample from the concentration of phosphate in the oxidized first sample, and using this difference to determine the concentration of phosphonate present in the aqueous solution; (G) comparing the concentration of phosphonate present in the solution to the new target concentration; and (H) if the concentration of phosphonate present in the solution is less than the new target concentration, increasing the concentration of phosphonate in the solution; or (H') if the concentration of phosphonate present in the solution is more than the new target concentration, reducing the concentration of phosphonate in the solution; (I) repeating (A)–(H) or (H'), thereby continually optimizing the concentration of phosphonate present in the solution. Optionally, one or more computers are used to automate this method.

In accordance with another aspect, the present invention provides an apparatus for oxidizing phosphonate present in an aqueous solution, comprising a recirculation loop comprising a pump, a digestion chamber and a venturi injector, wherein the pump pumps the aqueous solution through the digestion chamber and the venturi injector. The apparatus may further comprise an ozone generator connected to the venturi injector, wherein the venturi injector injects ozone from the ozone generator into the aqueous solution, and the digestion chamber may comprise a filling material which increases the surface area of the aqueous solution.

In accordance with another aspect, the present invention provides an apparatus for measuring the concentration of phosphate present in an aqueous solution, comprising (A) a recirculation loop comprising a pump, a digestion chamber and a venturi injector, wherein the pump pumps the aqueous solution through the digestion chamber and the venturi injector; and (B) a phosphate analyzer. The apparatus may further comprise an ozone generator connected to the venturi injector, wherein the venturi injector injects ozone from the ozone generator into the aqueous solution, and may further comprise a control valve between the recirculating loop and the phosphate analyzer. The digestion chamber may comprise a filling material which increases the surface area of the aqueous solution. Optionally, the apparatus comprises one or more computers controlling various aspects of the apparatus and determining the concentration of phosphonate present in the solution.

In accordance with another aspect, the present invention provides an apparatus for controlling the concentration of phosphate present in an aqueous solution, comprising (A) a recirculation loop comprising a pump, a digestion chamber and a venturi injector, wherein the pump pumps the aqueous solution through the digestion chamber and the venturi injector; (B) a phosphate analyzer; and (C) a source of phosphonate. The apparatus may further comprise an ozone generator connected to the venturi injector, wherein the venturi injector injects ozone from the ozone generator into the aqueous solution, may further comprise a control valve between the recirculating loop and the phosphate analyzer, and may further comprise a control valve between the aqueous solution and the source of phosphonate. Optionally, the apparatus comprises one or more computers controlling various aspects of the apparatus, determining the concentration of phosphonate present in the solution and comparing the concentration to a target concentration.

In accordance with another aspect, the present invention provides an apparatus for continually optimizing the concentration of phosphonate in an aqueous solution contained therein, comprising (A) a recirculation loop comprising a pump, a digestion chamber and a venturi injector, wherein the pump pumps the aqueous solution through the digestion chamber and the venturi injector; (B) a phosphate analyzer; (C) a source of phosphonate; and (D) a sensor, wherein the sensor monitors the apparatus for scale formation or corrosion. Optionally, the apparatus comprises one or more computers controlling various aspects of the apparatus, determining the concentration of phosphonate present in the solution, and comparing the concentration to a target concentration.

These and other objects and aspects of the invention will become apparent to the skilled artisan in view of the teachings contained herein.

BRIEF DESCRIPTION OF THE DRAWINGS

FIG. 1 is a diagram of an apparatus for determining the level of phosphonates in an aqueous solution.

FIG. 2 is a diagram of an apparatus for monitoring and controlling the level of phosphonates in an aqueous solution.

DETAILED DESCRIPTION OF THE INVENTION

The present invention is directed to a method and apparatus for oxidizing phosphonates present in an aqueous solution, and to methods and apparatus for determining, controlling and optimizing the concentration of phosphonates present in an aqueous solution. The methods are useful in any situation requiring the level of phosphonates in an aqueous solution to be controlled, such as water treatment systems, cooling water systems, boiling water systems and waste water systems. For convenience, the invention is described below with reference to water treatment systems; nevertheless, it is to be understood that the methods and apparatus described below are suitable for use in other aqueous systems where the concentration of phosphonates is to be controlled.

One aspect of the present invention provides a method for oxidizing phosphonates that does not rely on the use of chemical oxidizing agents such a potassium persulfate. In accordance with the present invention, an aqueous solution comprising one or more phosphonate compounds is reacted with ozone to oxidize the phosphonate to phosphate. Although ozone has been used in water treatment systems as a biocide, to kill bacteria, inhibit the growth of algae and destroy biofilms built up on the water treatment apparatus, see, e.g., Rice & Wilkes, *NACE Corrosion* 91, Paper #205 (1991); Hollingshad et al., *NACE Corrosion* 92, Paper #348 (1992), it has not heretofore been used in a method for oxidizing phosphonates in system water, or in a method for determining the concentration of phosphonates in system water.

When ozone is used in system water as a biocide, the ozone is provided throughout the water treatment system. Ozone's oxidation of phosphonates and other water treatment compounds is a disadvantage in these applications because the ozone destroys the compounds that were added to control corrosion and scale formation. See, e.g., Rice & Wilkes, supra; Hollingshad et al., supra. In accordance with the present invention, only a sample diverted from the system water is exposed to ozone. Accordingly, the negative effects of unwanted phosphonate oxidation (and the consequent loss of control of corrosion and scale formation) do not arise. Thus, in contrast to previous uses of ozone in water treatment systems, the present invention takes advantage of the oxidative effects of ozone on phosphonates without suffering from the drawbacks noted by Rice & Wilkes and Hollingshad.

Any phosphonate can be oxidized by ozone in accordance with the present invention. For example, organophosphonates typically used in a water treatment systems, such as hydroxyethylidene-1,1,- diphosphonic acid (HEDPA); 2-phosphononbutane-1,2,4-tricaraboxylic acid (PBTC); aminotri(methylenephosphonic acid) (AMP): hydoxyphosphonoacetic acid (HPA); and nitrotrimethylphosphonic acid (NTP), can be oxidized with ozone in accordance with the present invention. For convenience, the singular term "phosphonate" is used in the description below; however, it is to be understood that more than one phosphonate compound may be present in the aqueous solution, and that the present invention provides methods and apparatus for oxidizing, measuring, controlling and optimizing the total concentration of phosphonates in an aqueous solution, whether the phosphonate is provided as a single compound or as a mixture of compounds.

The ozone can be provided by means of any ozone generator, such as an ozone generator which uses UV light (254 nm) or electrical discharge to generate ozone from the air. An ozone generator which produces 0.01% ozone in air is suitable for use in the present invention. Ozone generators which produce higher concentrations of ozone also are useful; however, ozone has an unpleasant odor and can be hazardous with prolonged use. Accordingly, using generators which produce lower concentrations of ozone, such as 0.01%, may be preferred. Rice & Wilkes, supra, describes typical methods for generating ozone.

Molecular ozone ($O_3$) is relatively stable in high purity water when the pH is less than 6. Decomposition occurs at pH greater than 6, resulting in the formation of hydroxyl free radicals. The free radicals are more powerful oxidizing agents than ozone but also have a very short half life. The pH of the water (aqueous solution) in a water treatment system is typically in the range of 7.0–9.0. Accordingly, after the ozone is introduced to the aqueous solution, both ozone and hydroxyl radicals will be present. Rice & Wilkes, supra, describes the chemistry of ozone and ozone free radicals.

The aqueous solution can be reacted with ozone by any means. For example, a high concentration of ozone can be bubbled into the solution, or the solution can be circulated through a recirculation loop and the ozone introduced to the loop by a venturi injector which is in turn connected to an ozone generator. When a venturi injector is used, the ozone is automatically introduced to the loop when liquid flows through the injector. The injector also helps mix the ozone with the circulating aqueous solution. Recirculating the solution through the recirculation loop allows a sufficient concentration of ozone to build up in the aqueous solution to achieve phosphonate oxidation within a relatively short time, such as within about 5 to about 30 minutes.

In accordance with one embodiment of the invention, the recirculation loop comprises a digestion chamber for the oxidation reaction. Advantageously, the digestion chamber comprises a filling material which increases the surface area for the oxidation reaction, thereby increasing the efficiency of the reaction. For example, the digestion chamber may contain plastic mesh or plastic or glass beads, such as ¼-inch diameter beads, filling at least about 75% of the digestion chamber. When the digestion chamber is filled with beads, it may further comprise one or more small openings (for example, an opening with a diameter of from about ⅛ inch to about ¼ inch) to the atmosphere. The opening allows pressure inside the digestion chamber to be relieved, and the beads prevent the loss of ozone through the opening.

As discussed above, recirculation of the solution permits more complete oxidation of the phosphonate. The solution may be recirculated until, for example, at least about 80%, advantageously, at least about 90%, and more advantageously, at least about 95% of the phosphonate is oxidized. Some phosphonates are more resistant to oxidation and may require longer reaction times. The time needed to reach the desired degree of phosphonate oxidation can be determined, for example, by reacting a solution having a known concentration of phosphonate with ozone and monitoring the resulting phosphate level until the desired degree of oxidation (for example, 80%, 90%, 95% or 100%) has occurred. By this method, one skilled in the art can determine approximately how long it will take to reach the desired degree of phosphonate oxidation in the aqueous solution. A typical time is expected to be from about 10 to about 30 minutes, depending on the type of phosphonate, the ozone concentration and the water quality. See also Example 1 below.

FIG. 1 sets forth a diagram of an apparatus useful for carrying out this method of oxidizing phosphonate in an aqueous solution to determine the phosphonate concentration. The apparatus comprises a recirculation loop (102) comprising a pump (104), a venturi injector (106) and a digestion chamber (108). As discussed above, an ozone generator may be connected to the venturi injector. The digestion chamber may comprise a valve (110) to receive a sample of the aqueous solution, a filling material which increases the surface area for the oxidation reaction, an air vent (112) to relieve pressure, and a drain (114). The apparatus may further comprise a valve (116) connecting the apparatus to a phosphate analyzer (118).

This method for oxidizing phosphonate present in an aqueous solution can be used in a method for determining the concentration of phosphonate present in an aqueous solution. In accordance with this method, a sample of the aqueous solution is reacted with ozone to oxidize the phosphonate to phosphate, as described above. The concentration of phosphate present in this oxidized sample is measured, for example, by using a phosphate analyzer. This concentration is compared to the concentration of phosphate present in a non-oxidized sample of the aqueous solution, and the difference in the phosphate concentrations is used to determine the concentration of phosphonate present in the original, non-oxidized solution. Different phosphonates have different numbers of —PO$_3$H$_2$ groups per molecule. If these phosphonate are completely oxidized, they will release a corresponding number of orthophosphate groups. Accordingly, the type of phosphonates used in the aqueous solution will determine the ratio between the measured amount of phosphate and the corresponding amount of phosphonate compound.

Any means of determining the concentrations of phosphate can be used, including traditional grab sample methods. In accordance with one embodiment of the invention, a phosphate analyzer is used. Phosphate analyzers are known in the art. They usually rely on the colorometric reaction of phosphate with, for example, molybdovanadate, and subsequent measurement of the colored complex.

Their output typically is in the form of 4–20 mA signals proportional to the concentration of phosphate in the analyzed solution. Advantageously, the phosphate analyzer has two channels, one receiving a sample of non-oxidized system water (channel 1) and one receiving a sample of oxidized system water (channel 2). Alternatively, the phosphate analyzer has one channel, and alternately receives samples of non-oxidized and oxidized system water, for example, using a liquid stream multiplexing device. Single and multiple channel phosphate analyzers are known in the art. Referring now to FIG. 1, when an oxidizing recirculation loop (102) is used to oxidize the phosphonate, the phosphate analyzer (118) can receive a sample directly from the loop, for example, via a valve (116) connected to the digestion chamber (108).

The phosphate analyzer makes two measurements, one of a sample of non-oxidized system water (channel 1) and one of a sample of oxidized system water (channel 2). The signal from each channel is used to determine the phosphate concentration of each sample, and the phosphonate concentration of the system water is determined by subtracting the phosphate concentrations of the two samples (channel 2–channel 1). Advantageously, the phosphate analyzer is automated to take measurements of each channel at specified intervals. The phosphate analyzer also can be connected to a computer or other information processor which receives signals from the phosphate analyzer and calculates the concentration of phosphonate in the system water. This embodiment is shown in FIG. 1, where a computer (126) receives signals from channel 1 (120) and channel 2 (122) and calculates the concentration of phosphonate in the system water.

For accurate determinations of phosphonate concentrations, a sample of the aqueous solution is reacted with ozone until at least about 80%, advantageously at least about 90%, and more advantageously at least about 95% of the phosphonate is oxidized to phosphate before the concentration of phosphate in the oxidized sample is determined. After the time required to achieve the desired degree of oxidation has been determined (see above), this step can be automated, for example, by setting the valve between the recirculation loop and the analyzer to open at certain times, and/or by setting the analyzer to take measurements at certain times.

FIG. 1 sets forth an apparatus useful for carrying out this method. The oxidizing recirculation loop (102) of FIG. 1 is connected to a 2-channel phosphate analyzer (118) which receives samples of non-oxidized system water (channel 1 (120)) and oxidized water from the digestion chamber of the oxidizing recirculation loop (channel 2 (122)). The analyzer also may be connected to a source of reagent (124) which provides the colorometric reagent. As discussed above, the analyzer may be connected to a computer (126) which uses signals from the analyzer to calculate the concentration of phosphonate present in the system water.

This method for determining the concentration of phosphonate present in an aqueous solution can be fully automated. For example, the flow of system water into the oxidizing recirculation loop can be controlled such that a sample is sent into the loop at specified intervals, and the flow of oxidized solution from the loop to the phosphate analyzer can be controlled so that the solution goes to the analyzer after the desired degree of phosphonate oxidation has been achieved. As discussed above, the timing of the phosphate analyzer's measurements also can be controlled to coordinate the measurements of the non-oxidized and oxidized samples.

The present invention has several advantages over prior art methods. First, unlike grab sample methods which require chemical oxidizing agents and the performance of wet bench laboratory analysis, this method is readily subject to automation and does not require the use of dangerous, unstable chemical oxidizing agents. Accordingly, the present method is more efficient and less labor-intensive than prior art methods. It also can be more accurate than grab sample methods because it is less subject to human error. Moreover, unlike prior art tracer methods, the present method measures phosphonate levels directly, resulting in a more accurate determination of phosphonate levels than the tracer methods permit.

The methods of the present invention also can be used in a method for controlling the concentration of phosphonate present in an aqueous solution. In accordance with this embodiment of the invention, the concentration of phosphonate in the aqueous solution is determined by the method described above and compared with a predetermined target concentration. If the concentration is less than the target concentration, the concentration of phosphonate in the solution is increased. If the concentration is more than the target concentration, the concentration of phosphonate in the solution is decreased. The concentration of phosphonate can be adjusted, for example, by adding or not adding phosphonate to the solution or by increasing or decreasing the flow of phosphonate into the solution. This method can be automated, for example, with a computer or other information processing and control system determining the concentration of phosphonate present in the solution, comparing the concentration to a predetermined target concentration, and controlling the addition of phosphonate to the solution.

In some water treatment systems, phosphonate is added to the system water through a feed pump which is set to turn on and off at certain intervals. In accordance with the present invention, the feed pump also can be controlled by a computer which turns the pump off or on depending on whether the measured concentration of phosphonate is above or below the target level. Thus, the feed pump will be turned on and off in accordance with the preset schedule unless the computer determines that the pump should be turned on or off based on the measured concentration of phosphonate. Alternatively, a computer can control the flow of phosphonate into the system water, increasing or decreasing the flow rate to achieve the target concentration of phosphonate.

An apparatus for performing this method of controlling the phosphonate level is set forth in FIG. 2. The level of phosphonate in a water treatment system (202) is controlled by oxidizing a sample of the system water in a digestion chamber (204) using ozone supplied by an ozone generator (206). The oxidized system water is analyzed by a phosphate analyzer (208), which measures the concentration of phosphate in the oxidized system water, and also measures the concentration of phosphate in a sample of non-oxidized system water. This analyzer outputs these results in the form of signals related to the concentration of phosphate in the analyzed solution, for example 4–20 mA signals proportional to the concentration of phosphate in the analyzed solution. A computer (210) receives these signals, determines the concentration of phosphonate in the system water, and compares this concentration to a predetermined value. The computer controls a feed pump (212) which feeds phosphonate (214) into the system water (202).

The methods of the present invention also can be used in a method for optimizing the concentration of phosphonate present in an aqueous solution. In accordance with this embodiment of the invention, the apparatus used in the water treatment system is observed for scale formation and corrosion. Sensors which automatically measure scale and corrosion are known in the art. In accordance with this embodiment, if scale formation is observed, the target concentration of phosphonate in the solution is increased. If corrosion is observed, the target concentration of phosphonate in the solution is decreased. The concentration of phosphonate present in the solution is then controlled in accordance with the method set forth above, using the new target concentration as the predetermined target concentration. These steps can be repeated to effect continuous optimization of the concentration of phosphonate in the solution. As with the methods described above, most of the steps of this method can be automated, although a user probably would want to control when to use a new target concentration.

The embodiments of the invention are further illustrated through examples which show aspects of the invention in detail. These examples illustrate specific aspects of the invention and do not limit its scope.

EXAMPLES

Example 1

Determination of Oxidization Time

The time needed to effect substantially complete oxidation of phosphonate present in a water sample was determined as set forth below.

A ¼-inch PVC piping system comprising a recirculating loop comprising a pump, a venturi injector and a 2-inch diameter, 10-inch high cylindrical digestion chamber was used. About 500 mL of water containing about 8.5 ppm was introduced through a valve into the recirculation loop. The valve was closed, and the recirculating pump and ozone generator were started. The recirculation rate was approximately 6.0 L/min.

As the water sample recirculated it passed through the venturi injector, creating a vacuum at its side arm which draws ozone into the system. The internal structure of the venturi helps to effectively mix the incoming gas with the recirculating water sample. Using this system, an ozone level of greater than 0.1 ppm was achieved.

A phosphate analyzer was connected to the digestion chamber by another valve, and water sample was continuously introduced from the digestion chamber into the analyzer. The amount of phosphate present in the water sample was measured every minute, and the phosphate analyzer took seven minutes to analyze each sample. After about 12 minutes, the water sample measured by the phosphate analyzer contained about 8.5 ppm of phosphate, which corresponds to about 9.2 ppm of phosphonate. Accounting for the seven-minute delay attributed to the analyzer, it took about 5 minutes for substantially all of the phosphonate in the water sample to be oxidized to phosphate.

Example 2

Determination of Phosphonate Level

The apparatus described above is used to determine the concentration of phosphonate in the water of a water treatment system. About 500 mL of the water is introduced into the oxidizing recirculation loop. The water is recirculated for about 12 minutes, after which the ozone generator and recirculating pump are switched off. The valve is the opened, and oxidized sample flows from the recirculation loop to channel 2 of a 2-channel phosphate analyzer. After sufficient time is allowed for the sample to be introduced into the phosphate analyzer, the valve is closed and a drain valve is opened, draining the entire contents of the recirculation loop.

The 2-channel phosphate analyzer receives a sample of non-oxidized system water (channel 1) and oxidized system water from the recirculation loop (channel 2). For each measurement, the sample is reacted with molybdovanadate which forms a colored complex with phosphate. The amount of product formed is determined colorometrically and correlated to the concentration of phosphate present in the sample. The concentration of phosphonate present in the system water is determined by subtracting the concentration of phosphate in the non-oxidized sample from the concentration of phosphate in the oxidized sample.

Table 1 shows data for a cooling system operated over eight days in accordance with the method described above. The phosphonate level in the system water was varied by adding additional phosphonates or by reducing the phosphonate levels by increasing the blowdown rate of the system. Results from the phosphate analyzer were compared with results from a conventional wet-bench grab sample analysis.

TABLE 1

| Time (days) | Grab Sample | Phosphate Analyzer |
| --- | --- | --- |
| 1 | 2.7 | 2.5 |
| 2 | 3.5 | 3.6 |
| 3 | 2.1 | 2.3 |
| 4 | 5.4 | 5.4 |
| 5 | 6.5 | 6.0 |
| 6 | 5.8 | 5.7 |
| 7 | 5.4 | 5.0 |
| 8 | 5.8 | 5.2 |

Example 3

Controlling Phosphonate Level

A computer is used to measure the signal (4–20 mA current) from the two channels of the phosphate analyzer. The computer also controls a feed pump which feeds phosphonate into the system water. The feed pump is normally set to run for a preset period of time and then turn off. The computer also is able to turn the feed pump on or off.

The computer measures the difference between channel 2 and channel 1 to determine the concentration of phosphonate in the system water. The computer compares this concentration to a predetermined target concentration of phosphonate. If the measured concentration is less than the target concentration, the computer activates the feed pump. If the measured concentration is more than the target concentration, the computer turns off the feed pump.

What is claimed is:

1. A method for determining the concentration of phosphonate present in an aqueous solution, comprising
   (A) reacting a first sample of the solution with ozone, thereby forming an oxidized first sample comprising phosphate;
   (B) measuring the concentration of phosphate present in the oxidized first sample;
   (C) measuring the concentration of phosphate present in a second sample of the solution;
   (D) subtracting the concentration of phosphate in the second sample from the concentration of phosphate in the oxidized first sample, and using this difference to determine the concentration of phosphonate present in the aqueous solution.

2. The method of claim 1, wherein reacting the first sample with ozone comprises:
   (A) pumping the first sample through a recirculating loop;
   (B) introducing ozone into the loop through a venturi injector; and
   (C) digesting the first sample with ozone in a digestion chamber.

3. The method of claim 2, wherein the first sample is recirculated through the loop until at least about 90% of the phosphonate present in the sample is oxidized to phosphate.

4. The method of claim 2, wherein the first sample in the digestion chamber circulates through a filling material which increases the surface area of the first sample.

5. The method of claim 2, wherein the ozone is generated by an ozone generator connected to the venturi injector.

6. The method of claim 2, wherein the concentration of phosphate present in the oxidized first sample and the second sample is measured by an automated phosphate analyzer.

7. The method of claim 6, wherein a computer controls a control valve between the recirculation loop and the phosphate analyzer.

8. The method of claim 7, wherein a computer receives signals from the phosphate analyzer and determines the concentration of phosphonate present in the solution.

9. The method of claim 6, wherein the concentration of phosphonate present in the solution is determined by a computer.

10. A method for determining the concentration of phosphonate present in an aqueous solution,.:comprising:
    (A) diverting a first sample of the aqueous solution into a recirculation loop;
    (B) introducing ozone into the loop through a venturi injector;
    (C) digesting the first sample with ozone in a digestion chamber;
    (D) recirculating the first sample through the recirculation loop until at least about 90% of the phosphonate present in the first sample is oxidized to phosphate;
    (E) introducing the oxidized first sample to a phosphate analyzer;
    (F) measuring the concentration of phosphate present in the oxidized first sample;
    (G) introducing a second sample of the aqueous solution into the phosphate analyzer;
    (H) measuring the concentration of phosphate present in the second sample;
    (I) subtracting the concentration of phosphate in the second sample from the concentration of phosphate in the oxidized first sample, and using this difference to determine the concentration of phosphonate present in the aqueous solution.

11. A method for controlling the concentration of phosphonate present in an aqueous solution, comprising:
    (A) reacting a first sample of the aqueous solution with ozone, thereby forming an oxidized first sample comprising phosphate;
    (B) introducing the oxidized first sample to a phosphate analyzer;
    (C) measuring the concentration of phosphate present in the oxidized first sample;
    (D) introducing a second sample of the aqueous solution into the phosphate analyzer;
    (E) measuring the concentration of phosphate present in a second sample of the aqueous solution;
    (F) subtracting the concentration of phosphate in the second sample from the concentration of phosphate in the oxidized first sample, and using this difference to determine the concentration of phosphonate present in the aqueous solution;
    (G) comparing the concentration of phosphonate present in the solution to a predetermined target concentration; and
    (H) if the concentration of phosphonate present in the solution is less than the target concentration, increasing the concentration of phosphonate in the solution; or
    (H') if the concentration of phosphonate present in the solution is more than the target concentration, reducing the concentration of phosphonate in the solution.

12. The method of claim 11, wherein the concentration of phosphonate present in the solution is compared to the predetermined target concentration by a computer.

13. The method of claim 12, wherein the computer:
    receives signals from the phosphate analyzer indicating the concentration of phosphate present in the first oxidized sample and the concentration of phosphate present in the second sample;
    uses the signals to determine the concentration of phosphonate present in the solution; and
    compares the concentration of phosphonate present in the solution to a predetermined target concentration.

14. The method of claim 11, wherein a computer is used to increase or decrease the concentration of phosphonate in the solution.

15. The method of claim 14, wherein the computer controls a control valve between the solution and a source of phosphonate.

16. The method of claim 15, wherein the computer:
    receives signals from the phosphate analyzer indicating the concentration of phosphate present in the first oxidized sample and the concentration of phosphate present in the second sample;
    uses the signals to determine the concentration of phosphonate present in the solution;
    compares the concentration of phosphonate present in the solution to a predetermined target concentration; and
    if the concentration is less than the target concentration, adjusts the control valve to increase the concentration of phosphonate in the solution; or if the concentration is greater than the target concentration, adjusts the control valve to decrease the concentration of phosphonate in the solution.

17. A method for continually optimizing the concentration of phosphonate in an aqueous solution contained in an apparatus, comprising:

(A) observing the apparatus for scale formation or corrosion;

(B) if scale formation is observed, increasing a predetermined target concentration of phosphonate present in the solution to establish a new target concentration; or (B') if corrosion is observed, decreasing a predetermined target concentration of phosphonate present in the solution to establish a new target concentration;

(C) reacting a first sample of the aqueous solution with ozone, thereby forming an oxidized first sample comprising phosphate;

(D) measuring the concentration of phosphate present in the oxidized first sample;

(E) measuring the concentration of phosphate present in a second sample of the aqueous solution;

(F) subtracting the concentration of phosphate in the second sample from the concentration of phosphate in the oxidized first sample, and using this difference to determine the concentration of phosphonate present in the aqueous solution;

(G) comparing the concentration of phosphonate present in the solution to the new target concentration; and (H) if the concentration of phosphonate present in the solution is less than the new target concentration, increasing the concentration of phosphonate in the solution; or (H') if the concentration of phosphonate present in the solution is more than the new target concentration, reducing the concentration of phosphonate in the solution; and (I) repeating (A)–(H) or (H'), thereby continually optimizing the concentration of phosphonate present in the solution.

18. The method of claim 17, wherein a sensor is used to automatically observe the apparatus for scale formation or corrosion.

* * * * *